United States Patent
Yakovlev et al.

(10) Patent No.: US 10,444,236 B2
(45) Date of Patent: Oct. 15, 2019

(54) METHOD OF DETECTION OF PROTEOLYSIS PRODUCTS IN PLASMA AND A DIAGNOSTIC SYSTEM FOR ITS APPLICATION

(71) Applicants: Vasily Nikolaevich Yakovlev, Moscow (RU); Alexei Alexeevich Kanaev, Moscow (RU); Rustam Raisovich Suleimanov, Moscow (RU)

(72) Inventors: Vasily Nikolaevich Yakovlev, Moscow (RU); Alexei Alexeevich Kanaev, Moscow (RU); Rustam Raisovich Suleimanov, Moscow (RU)

(*) Notice: Subject to any disclaimer, the term of this patent is extended or adjusted under 35 U.S.C. 154(b) by 323 days.

(21) Appl. No.: 15/304,896

(22) PCT Filed: Aug. 25, 2016

(86) PCT No.: PCT/RU2016/000573
§ 371 (c)(1),
(2) Date: Oct. 18, 2016

(87) PCT Pub. No.: WO2017/034442
PCT Pub. Date: Mar. 2, 2017

(65) Prior Publication Data
US 2017/0176442 A1  Jun. 22, 2017

(30) Foreign Application Priority Data
Aug. 25, 2015 (RU) ............... 20150135793

(51) Int. Cl.
*G01N 33/50* (2006.01)
*G01N 33/574* (2006.01)
*G01N 33/564* (2006.01)
*G01N 33/68* (2006.01)

(52) U.S. Cl.
CPC ..... *G01N 33/57434* (2013.01); *G01N 33/564* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 7,384,635 B2* | 6/2008 | Holm | C07K 14/415 424/184.1 |
| 2012/0009650 A1* | 1/2012 | Koepf | C12N 9/6435 435/217 |

OTHER PUBLICATIONS

Viken et al., Influence on Antibody Recognition of Amino Acid Subtitutions in the Cleft of HLA-DQ2 Molecules, Human Immunology, 44, 1995, pp. 63-69. (Year: 1995).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Harpel et al., Binding and Activation of Plasminogen on Immobilized Immunoglobulin G, The Journal of Biological Chemistry, vol. 264, No. 1, Jan. 1989, pp. 616-624. (Year: 1989).*
Carlsson et al., Kringle 2 Mediates High Affinity Binding of Plasminogen to an Internal Sequence in Streptococcal Surface Protein PAM, The Journal of Biological Chemistry, vol. 273, No. 38, Sep. 1998, pp. 24420-24424. (Year: 1998).*

* cited by examiner

*Primary Examiner* — Gary Counts
(74) *Attorney, Agent, or Firm* — Nadya Reingand; Yan Hankin

(57) ABSTRACT

Immunological diagnostic methods that use the whole-length molecule of plasminogen or its peptide fragments as universal detectors of proteolysis products having a C-terminal lysine are proposed. The method of this immunological diagnostic is to identify the human diseases associated with increased activity of proteolytic enzymes. A diagnostic test system comprised of a detector—the full-length molecule and its presented peptide fragments—is disclosed. The technical result includes achieving the required degree of dissociation of the antigen-antibody complex in a sample from the subject, as well as changing the conformation of proteins using an incubation buffer containing organic solvents in the disclosed ratios, that can significantly increase the sensitivity of the method for determining the concentration of proteolytic fragments with a C-terminal lysine binding with plasminogen or fragments thereof.

14 Claims, 2 Drawing Sheets
Specification includes a Sequence Listing.

METHOD OF DETECTION OF PROTEOLYSIS PRODUCTS IN PLASMA AND A DIAGNOSTIC SYSTEM FOR ITS APPLICATION

CROSS-REFERENCE TO RELATED APPLICATIONS

The present application is a U.S. National stage application from the PCT application PCT/RU2016/000573 filed on Aug. 25, 2016, which claims priority to Russian patent application RU2015135793 filed on Aug. 25, 2015.

FIELD OF INVENTION

The present invention relates to the fields of medicine and immunology. In particular, this invention relates to immunological diagnostic methods that utilize the full-length molecule of plasminogen or its peptide fragments which may be used as universal detectors of proteolytic products having a C-terminal lysine in an immunological diagnostic to identify the human diseases associated with increased activity of proteolytic enzymes. The group of inventions also relates to a diagnostic test system utilizing as a detector the full-length molecule and its presented peptide fragments.

TERMINOLOGY

Technical and scientific terms used in the description have the same meaning and value that are commonly used in the relevant areas of science and technology.

The term "antigen" as used herein refers to a protein or fragments thereof, capable of binding antibodies.

The term "detector" refers to a peptide sequence capable of binding to the C-terminal lysine of proteins formed after proteolysis.

The term "kringle" refers to a protein domain having a structure stabilized by three disulfide bonds.

The term "domain" refers to a part of a protein characterized by certain structural or functional properties.

The term "analysis" refers to methods of identifying of the molecular compounds, comprising the steps of: (a) the interaction with the antigen within a biological sample under suitable conditions to form an antigen-antibody complex; and (b) the detection of these complexes.

The term "marker" refers to particular molecular compounds of a specific structure, the presence of which in human tissue samples is associated with a a specific range of diseases.

The term "epitope" herein refers to a region of a protein molecule which is capable of interacting with the antibody.

The term "ligand" herein refers to a protein molecule which is capable of forming a non-covalent bond with another protein molecule.

The term "diagnostic test" is the detection of a diagnostic determinant using a specific laboratory method, the analytical parameters of which remain constant.

BACKGROUND

There is presently unclear need for the development of new markers for the diagnosis of diseases associated with elevated levels of proteolytic cleavage of proteins in the body, particularly those involved in the early stages of tumorigenesis. Tumor development is accompanied by a high level of proteolytic activity (Al-Majid S., Waters H. The biological mechanisms of cancer-related skeletal muscle wasting: the role of progressive resistance exercise/Biol. Res. Nurs. 2008. Vol. 10, No 1. pp. 7-20). Indeed, the level of proteolytic activity is currently considered one of the factors of carcinogenesis (Bashir T., Pagano M. Aberrant ubiquitin-mediated proteolysis of cell cycle regulatory proteins and oncogenesis/Adv. Cancer. Res. 2003. Vol. 88. pp. 101-144). Several types of proteases are involved in the process of carcinogenesis by enhancing the proliferation, invasion, and metastasis of tumor cells (Chilingirov AD proteolysis inhibitor effect on some bacterial pathogens, and for inflammatory processes/Pat. Fiziol. And experimental. Therapy. 1997. No 3. C. 37-39; Søreide K. Proteinase-activated receptor 2 (PAR-2) in gastrointestinal and pancreatic pathophysiology, inflammation and neoplasia/Scand. J. Gastroenterol. 2008. Vol. 43, No 8. pp. 902-909). Of these, serine proteases are reported to most significantly contribute to the process of carcinogenesis (Zorio E., Gilabert-Estellés J., España F., Ramón LA, Cosín R., Estellés A. Fibrinolysis: the key to new pathogenetic mechanisms/Curr. Med. Chem. 2008. Vol. 15, No 9, pp. 923-929).

Serine proteases usually cleave peptide bonds between positively charged amino acids lysine and arginine, as well as the esters and amides of these amino acids (Fersht E. The structure and mechanism of action of enzymes. Ed. Kurganova BI Moscow, "Mir" 1980. 432 pp . . . ). To date, some authors have shown that the products of proteolytic activity can serve as a universal marker, the detection of which is associated with various autoimmune and oncogenic processes. For example, the high content of the products of proteolytic cleavage of immunoglobulins can be used as a marker of autoimmune disease or cancer (Robert Jordan et al, U.S. Ser. No. 08/501,907). In that work, the authors proposed a method for the detection of proteolytic cleavage of immunoglobulins using polyclonal and monoclonal antibodies. Other authors presented data on the specific proteolysis of immunoglobulins by plasmin (Peter S. Harpel et al The J. of biological chemistry Vol. 264, No. 1, Issue of January 5, pp. 616-624 (1989)). Following cleavage, the immunoglobulin molecule was shown to specifically interact with plasminogen due to the presence of a C-terminal lysine.

Plasmin, a trypsin-like serine protease, is usually generated by the activation of plasminogen by streptokinase, urokinase or tissue plasminogen activator (tPA). It is well known that plasminogen exhibits fibrinolytic activity and can block clot formation by binding to the C-terminal lysine residues of fibrin and the proteolysis of fibrin fibers. Both plasminogen and plasmin bind to fibrin through kringle regions, each of which is a triple loop region formed by disulfide bonds. Kringles K1, K2, K3, K4, and $K_5$ have a strong affinity for lysine.

a. The participation of the C-terminal lysine in protein binding to plasminogen has been demonstrated by Marco Candela et al., (Binding of Human Plasminogen to *Bifidobacterium*, Journal of bacteriology, August 2007, p. 5929-5936). In this study, proteins which bind to plasminogen were treated with carboxypeptidase B, which specifically cleaves only C-terminal lysine and arginine. After this treatment, the proteins lost their ability to bind to plasminogen, indicating that C-terminal lysine participation is essential for the binding to plasminogen and its fragments.

The plasminogen/plasmin system not only takes an active part in the process of fibrinolysis, but has also been shown to be closely associated with angiogenesis and carcinogenesis. Interestingly, some products of plasminogen degradation may be more active than the intact plasminogen molecule in the processes of angiogenesis and carcinogenesis. (Y G Klys, et all, Proteolytic plasminogen derivatives in the development of malignancies, Oncology, V 12, No. 1, 2010). The following variants of fragments of plasminogen in the plasma have been described: K1-3; K2-3; K1-4; K1-4, 5; and K1-5 (Perri S, Martineau D, Francois M, et al. Plasminogen kringle 5 blocks tumor progression by antiangiogenic and proinflammatory pathways. Mol Cancer Ther 2007; 6: pp. 441-449). It has previously been shown that all kringle domains are actively involved in angiogenesis and carcinogenesis. The activity of the first four kringles (K1-4) is the best-studied—they play a role in angiogenesis. For example, this sequence of kringle domains is found in angiostatin (Francis J. Castellino, Victoria A. Ploplis, Structure and function of the plasminogen/plasmin system, ThrombHaemost 2005; 93: pp. 647-54; C. Boccaccio and Paolo M. Comoglio Cancer Res 2005; 65 (19): pp. 8579-82; Rijken D C, Lijnen H R. New insights into the molecular mechanisms of the fibrinolytic system. J Thromb. Haemost 2009; 7: pp. 4-13). The activation of plasminogen and some of the other serine proteases leads to an increase in the amount of C-terminal lysine containing protein proteolysis products during carcinogenesis. Since the intact plasminogen molecule as well as its fragments has lysine binding sites, they can bind the degradation products with a C-terminal lysine generated by serine proteases and be used as detectors of the process of carcinogenesis and other pathological processes. This detector has universal properties compared with other proposed methods of detecting degradation products, which require using monoclonal antibodies specific for each product of proteolysis.

The detection of the products of proteolysis in plasma in both human and animal samples can be performed using enzyme-linked immunosorbent assay (ELISA), where the plasminogen molecule or its fragments are used as a detector. The ELISA was first developed in 1971 and currently, an extensive range of types and modifications of ELISA are used. The basic principles of ELISA, regardless of modifications, are as follows:

1. At the first stage of the reaction, antigens or antibodies are adsorbed onto a solid phase. The reagents or compounds not bound to the solid phase are easily removed by washing.
2. Test samples and controls are incubated in the coated wells—thus, immune complexes can be formed on the surface of the solid phase. Unbound components are removed by washing.
3. Antibody-enzyme or antigen-enzyme conjugates, which bind a complementary site on the antigen (or antibody) on the solid phase are then added. Their binding is detected via a colorimetric reaction after the adding of the substrate for the conjugated enzyme. This reaction can be stopped and optical density can be measured.

The levels of the immunoglobulin and other proteins after proteolysis are determined using an indirect ELISA. The wells are coated by antibodies to the desired protein (antigen) and incubated with the serum (plasma) samples or other biological material from the patient (cerebrospinal fluid, saliva, etc.). Specific antigens bound to antibodies at the solid phase are detected using a second antibody-enzyme conjugate to another epitope of the antigen. Depending on the purpose of the assay, different antigens are used, either with antibodies universal for all isotypes or specific to certain classes and subclasses of immunoglobulins. The main advantage of this method is in the versatility of the conjugate. This reaction is also methodologically simple.

The main stages of an indirect ELISA for the determination of specific antigens (or antibodies) in the sample are as follows:

1. The antigen, or the ligand (antibody) is adsorbed onto a solid phase, and then washed free of unbound components.
2. The free binding sites are blocked. The wash step is repeated.
3. The samples are added to the wells, incubated and then the wells are washed to remove unbound components. Samples serving as positive and negative controls are incubated in parallel wells.
4. The antibody-enzyme or antigen-enzyme conjugate is added at a working dilution, incubated and the unbound components are washed away.
5. The colorimetric substrate is added. The color reaction is stopped by adding a stop solution.
6. The optical density is measure on a reader.

Under optimum conditions, this method has both a high specificity and a high sensitivity. It can detect nanogram quantities of antigen (or antibody) in serum (or plasma). However, existing methods of immunoassay detection of antigen have a limitation associated with the fact that some antigen in the sample can be present in a complex with other proteins. This complex does not bind to the solid phase, that masks the true concentration of the antigen in the sample. At sufficiently high concentrations of the complex, false negatives may result. To determine the true concentration of antigens, the dissociation of this complex is required. In a previous study of the binding properties of the antigen-antibody complex, it was demonstrated that the use of different organic solvents can increase the sensitivity of the reaction (Mohd. Rehan, HinaYounus, Int. J. of Biol. Macromolecules, Effect of organic solvents on the conformation ant interaction of catalase and anticatalase antibodies).

We have developed a method and a test system with an increased sensitivity of detection of proteolytic products. In the claimed invention, both full-length plasminogen molecules as well as plasminogen fragments of a defined structure are used as antigens and detectors. The claimed invention furthermore uses organic components to detect C-terminal lysine containing proteolysis fragments of immunoglobulin and other protein, which significantly increases the sensitivity of the diagnostic test system.

DISCLOSURE OF THE INVENTION

Increased level of immunoglobulins and other proteins having a C-terminal lysine residue after proteolysis and that can bind to plasminogen or fragments thereof, can serve as diagnostic markers of diseases associated with elevated levels of proteolytic fragments of immunoglobulin and other proteins.

The inventors hypothesized that serine proteases are activated in the area of chronic inflammation associated with tumor progression, which leads to the accumulation of proteolitic products with C-terminal lysines. These proteolytic products enter circulation and their amounts can be determined by immunoanalysis. Experiments performed by the inventors have shown that proteolytic products with a C-terminal lysine can be detected using plasminogen or fragments thereof. Thus, the elevated levels of proteolytic products with a C-terminal lysine in blood are a marker of disease associated with elevated levels of proteolytic products having a C-terminal lysine, and the measurement of the levels of these proteins in blood can be used as a diagnostic indicator of a developing disease process.

To increase the sensitivity of detection of the concentration of proteolytic fragments with a C-terminal lysine residue, the inventors developed novel buffer solutions which include a number of organic solvents (dimethylsulfoxide, dimetlformamid, methanol, ethanol, propanol, propanol-2, acetone, acetonitrile, chloroform, ethylene glycol, N-methylpropanamide. The fragment of plasminogen in the claimed test system is selected from the list in Table 1. The control sample used in the test system is a sample from a healthy subject.

TABLE 1

Frangments of plasminogen having kringle structures.

| Peptide | kDa | Kringles | No SEQ ID |
|---|---|---|---|
| $Glu^1-Asn^{791}$ | 98 | Glu Plasminogen | SEQ ID NO: 1 |
| $Lys^{78}-Asn^{791}$ | 83,5-84 | Lys-Plasminogen | SEQ ID NO: 2 |
| $Glu^1-Arg^{561}$ | 65 | Glu-Heavy chain (Glu-H) | SEQ ID NO: 3 |
| $Lys^{78}-Arg^{561}$ | 59 | Lys-Heavy chain (Lys-H) | SEQ ID NO: 4 |
| $Val^{562}-Asn^{791}$ | 25(26,3) | Light chain(L) | SEQ ID NO: 5 |
| $Tyr^{80}-Ala^{440}$ | 51-54 | K1-4 ($Tyr^{80}-Ala^{440}$) | SEQ ID NO: 6 |
| $Tyr^{80}-Val^{338}$ | 41 | K1-3 ($Tyr^{80}-Val^{338}$) | SEQ ID NO: 7 |
| $Tyr^{80}-Val^{354}$ | 44 | K1-3 ($Tyr^{80}-Val^{354}$) | SEQ ID NO: 8 |
| $Asn^{60}-Pro^{447}$ | 55 | K1-4 ($Asn^{60}-Pro^{447}$) | SEQ ID NO: 9 |
| $Lys^{78}-Pro^{447}$ | 58 | K1-4 ($Lys^{78}-Pro^{447}$) | SEQ ID NO: 10 |
| $Lys^{78}-Pro^{446}$ | 58 | K1-4 ($Lys^{78}-Pro^{446}$) | SEQ ID NO: 11 |
| $Lys^{78}-Lys^{468}$ | 61 | K1-4 ($Lys^{78}-Lys^{468}$) | SEQ ID NO: 12 |
| $Lys^{78}-Arg^{530}$ | 66,60,57 | K1-4,5 ($Lys^{78}-Arg^{530}$) | SEQ ID NO: 13 |
| $Val^{355}-Phe^{546}$ | 22 | K4-5 ($Val^{355}-Phe^{546}$) | SEQ ID NO: 14 |
| $Tyr^{80}-Glu^{164}$ | 9,81 | K1 ($Tyr^{80}-Glu^{164}$) | SEQ ID NO: 15 |
| $Cys^{165}-Val^{338}$ | 21 | K2-3 ($Cys^{165}-Val^{338}$) | SEQ ID NO: 16 |
| $Val^{354}-Ala^{440}$ | 10-12 | K4 ($Val^{354}-Ala^{440}$) | SEQ ID NO: 17 |
| $Ser^{441}-Fhe^{546}$ | 12 | K5 ($Ser^{441}-Fhe^{546}$) | SEQ ID NO: 18 |
| $Val^{442}-Arg^{561}$ | 12 | K5 ($Val^{442}-Arg^{561}$) | SEQ ID NO: 19 |
| $Val^{442}-Asn^{791}$ | 40(38) | miniplasmin | SEQ ID NO: 20 | dimetlformamid, methanol, ethanol, propanol, propanol-2, acetone, acetonitrile, chloroform, ethylene glycol, N-methylpropanamide) to decrease the hydrophobic interactions between molecules. To date, there are no reports in the published literature of using the proposed organic solvents in incubation buffers to determine the level of proteolytic fragments with a C-terminal lysine.

The inventors describe a new method of detection of the concentration of proteolytic fragments having a C-terminal lysine in blood, which is a diagnostic test system for identifying subjects with a high concentration of proteolytic fragments with a C-terminal lysine that are capable of binding to plasminogen or fragments thereof. This diagnostic test system is comprised of an incubation buffer prepared with organic solvents, the antigen or the detector—a full length plasminogen or its fragments containing at least one sequense of SEQ ID NO: 1-20, and the control sample (C). The composition of the incubation buffer includes at least one component selected from the following group of solvents: dimethylsulfoxide, dimetlformamid, methanol, ethanol, propanol, propanol-2, acetone, acetonitrile, chloroform, ethylene glycol, N-methylpropanamide. The fragment of plasminogen in the claimed test system is selected from the list in Table 1. The control sample used in the test system is a sample from a healthy subject.

Plasminogen and/or the fragments thereof may be immobilized on a solid support which may also be included in the test system. The antibodies to the products of proteolysis with a C-terminal lysine can also be immobilized on the solid support and, in turn, bind plasminogen or fragments thereof containing at least one sequence of SEQ ID NO: 1-20. To assess the concentration of proteolytic fragments with a C-terminal lysine in blood using the claimed test system, the fragment of plasminogen is selected from the list in Table 1. The identification of proteolytic fragments having a C-terminal lysine is performed via an immune reaction, followed by a subsequent colorimetric, fluorescence, or conductivity methods of detection. Thus, the concentration of proteolytic fragments with a C-terminal lysine can be determined using any known methods of detection: colorimetric, fluorescent or conductometric. A concentration of proteolytic fragments with a C-terminal lysine in the test sample which is 30% higher compared to the control sample is taken to indicate the presence of a pathological process in the subject.

The claimed test system can be used to identify subjects with risk of having of cancer or autoimmune diseases. To this end, the method allows the use of the claimed diagnostic test system for identifying subjects with increased levels of proteolytic fragments with a C-terminal lysine that are capable of binding to plasminogen or fragments thereof. To detect elevated levels of proteolytic fragments with a C-terminal lysine, a sample from a subject is compared to a control sample from a healthy donor. In the claimed diagnostic test system, the authors show a technical result in the achievement of the required degree of dissociation of the antigen-antibody complex in the subject sample, as well as in changing the conformation of proteins using the incubation buffer containing organic solvents in the disclosed ratios, which allows a significant enhancement of the sensitivity of detection of concentration of proteolytic fragments with a C-terminal lysine that are capable of binding to plasminogen or fragments thereof.

Ligands and Detectors for the Immunoassay

Plasminogen is a single-chain glycoprotein present in plasma at a concentration of about 2 μM (Wohl et al., Thromb. Res. 27:523-535, 1982; Kang et al., Trends Cardiovasc. Med. 90:92-102, 1999). Plasminogen contains 791 amino acid residues and 24 disulfide bonds. The protein consists of a single polypeptide chain, with an N-terminal glutamine and a C-terminal asparagine. It contains 2%-3% carbohydrates, which are localized within the heavy chain. Oligosaccharides are attached to Asp288 and Tre345. Plasminogen is a precursor of plasmin, which is formed by the cleavage of plasminogen between Arg-561 and Val-562 by tissue plasminogen activator (tPA) or urokinase-type plasminogen activator. In the process of activation of plasminogen, a bond between Arg560 and Val561 is cleaved; light and heavy chain are formed, connected by disulfide bonds. The light chain (Val561-Asn790) has an active protease site, including the amino acid sequence of Ser-His-Asp. The plasmin heavy chain (Lys78-Arg560) has five triple disulfide-linked loops known as kringle regions—or kringle domains—which are compact globular structures with a hydrophobic core. These structures are involved in the process of protein interaction in blood clotting. Both plasminogen and plasmin bind to fibrin through amino-terminal kringle regions, each of which is a triple loop region formed and fixed by disulfide bonds. Kringles of the heavy chain consist of K1, K2, K3, K4, and K5. Kringles 1-4 have domains which have a strong affinity for lysine, ε-aminocaproic acid, parabens, and other on-carbon amino acids having antifibrinolytic properties. Lysine binding sites (LBS) play an important role in the interaction between plasmin (plasminogen) and fibrin, as well as plasmin and its inhibitor—α2-AP (antiplasmin). Any fragment of plasminogen containing a kringle, regardless of whether it is a product of natural cleavage in vivo or a result of cleavage of plasminogen in vitro (e.g., by enzymatic action) can be used to detect proteolytic fragments with a C-terminal lysine. To assess the concentration of proteolytic fragments with a C-terminal lysine in diseases associated with the accumulation of such fragments, either plasminogen fragments or the full-length plasminogen molecule can be used as detectors. Specifically, a full-length plasminogen molecule, its heavy chain alone, as well as any of its fragments containing a kringle domain may be used as ligands, immobilized on a solid phase, to determine the concentration of proteolytic fragments with a C-terminal lysine in blood samples.

These ligands and detectors can be either native Glu-plasminogen or its proteolytic derivatives may be prepared using genetic engineering techniques, by synthesis of a recombinant peptide in bacterial or eukaryotic expression systems. The recombinant ligands and detectors correspond to the amino acid sequence of human plasminogen. Specifically, the ligand and the detector for the disclosed invention are the full-length plasminogen and its fragments presented in Table 1.

The inventors were the first to describe and confirm that plasminogen or the fragments thereof may be used as ligands and detectors to determine the concentration of proteolytic fragments having a C-terminal lysine in a sample of human blood plasma by enzyme immunoassay and the result of this assay can be used as an important diagnostic sign to detect the presence of a pathological process in the subject.

The authors were the first to have applied a method of processing of plasma samples using dimethylsulfoxide, dimetlformamid, methanol, ethanol, propanol, propanol-2, acetone, acetonitrile, chloroform, ethylene glycol, N-methylpropanamide in an incubation buffer composition, that allows to increase the sensitivity of the method, compared to the methods, where the incubation buffer solution does not include the proposed components.

Despite the fact that the proposed method of detection is based on the use of specific well-defined polypeptides and buffer solution components, it should be clear to any qualified specialist in this scientific field that other proteins and peptides having the same composition of amino acid sequences and any combination of the proposed components in an incubation buffer identical to those in the disclosed invention can be used in an analogous fashion.

It should be clear to all qualified persons in this scientific field that the antigens and detectors in the present invention may be replaced by any amino acid having an polypeptide homology of more than 80% with the proposed polypeptides, since the replacement of amino acids that does not alter the structure of the kringle domains will not be an obstacle to the detection of proteolytic fragments having a C-terminal lysine.

Table 1 describes the various polypeptides—the derivatives of plasminogen that can be used for the enzyme immunoassay reaction with samples of human blood plasma for identification of proteolytic fragments with a C-terminal lysine.

Table 2 shows the different organic components in the buffer used for the preliminary treatment of plasma samples. The composition of the incubation buffer of can include anywhere from 5-25% of the organic components shown in Table 2 in 0.15 M Tris-HCl pH 8.8.

TABLE 2

Solvent of buffer for incubation

| | Solvents | Preferred Concentration |
|---|---|---|
| 1. | dimethylsulfoxide | 20% |
| 2. | dimethylformamide | 20% |
| 3 | methanol | 20% |
| 4. | ethanol | 20% |
| 5. | propanol | 20% |
| 6. | propanol-2 | 20% |
| 7. | acetone | 20% |
| 8. | acetonitrile | 20% |
| 9. | chloroform | 20% |
| 10. | ethylene glycol | 20% |
| 11. | N-methylpropanamide | 20% |

Filled arrows indicate the cleavage sites for: (a) the release of the signal peptide, which is required for the production of the mature form of the protein (Glu-plasminogen); (b) the release of the activation peptide (Glu'-Lys$^{77}$) resulting in the conversion of Glu'-plasminogen to Lys$^{78}$-plasminogen or Glu'-Plasmin to Lys$^{78}$-Plasmin; (c) the activation of plasminogen to plasmin by the cleavage of the Arg$^{561}$-Val$^{562}$ peptide bond. Unfilled arrows indicate the introns in the gene sequence. Triangles identify the N-linked oligosaccharide site at sequence position 289 and the O-linked glycan at position 346. The catalytic triad, His$^{603}$, Asp$^{741}$, and Ser$^{741}$, is also indicated by anasterisk (*). Disulfide bonds are depicted by heavy lines. A filled diamond (♦) indicates a phosphorylation site.

The 20 amino acids and the abbreviations used are as follows:

```
alanine-ala-A; arginine-arg-R; asparagine-asn-N;
aspartic acid-asp-D; cysteine-cys-C; glutamine-
gln-Q; glutamic acid-glu-E; glycine-gly-G;
histidine-his-H; isoleucine-Ile-I; leucine-leu-L;
lysine-lys-K; methionine-met-M; phenylalanine-phe-
F; proline-pro-P; serine-ser-S; threonine-thr-T;
trytophan-trp-W; tyrosine-tyr-Y; valine-val-V.
```

Figure 1:
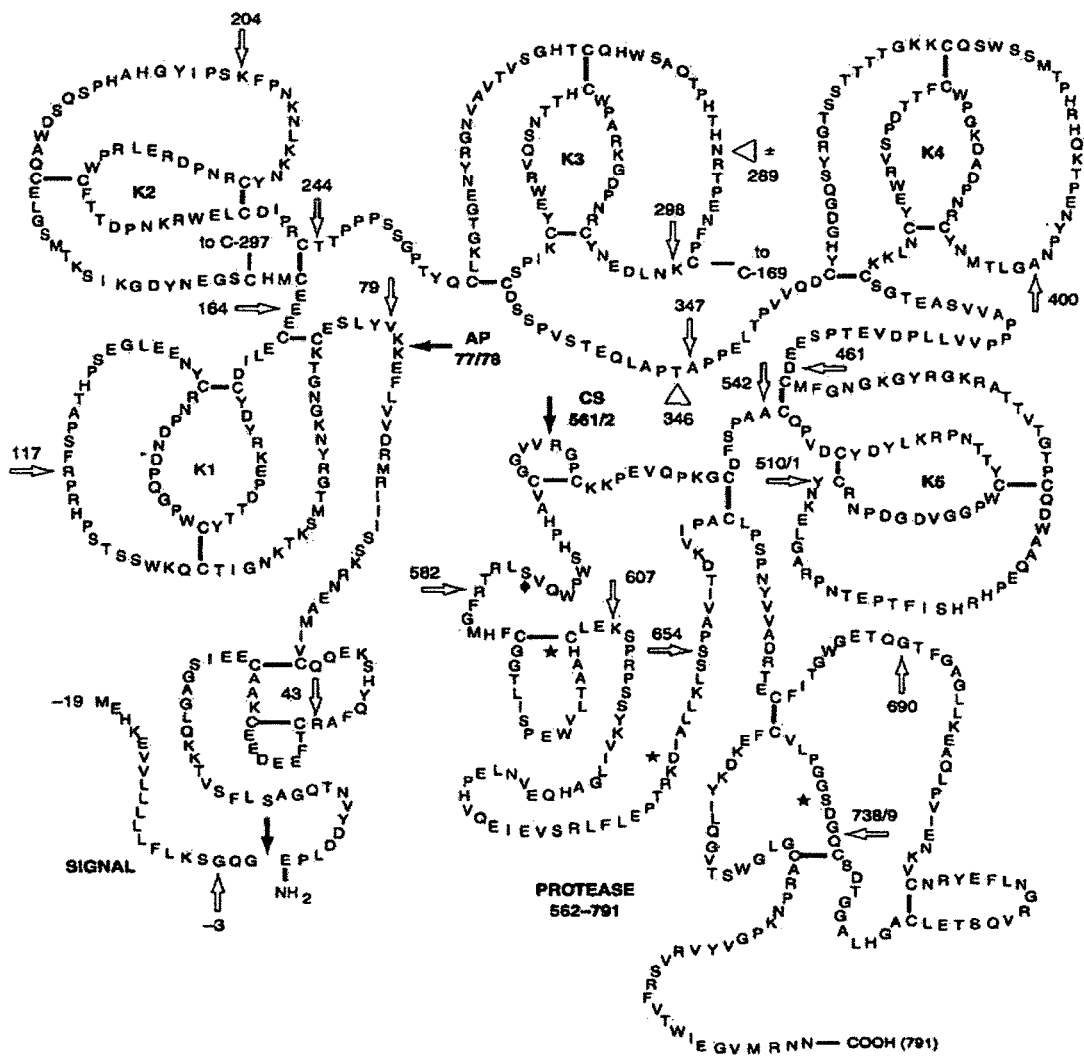
FIG. 1. The primary structure of human plasminogen.
Figure 2:
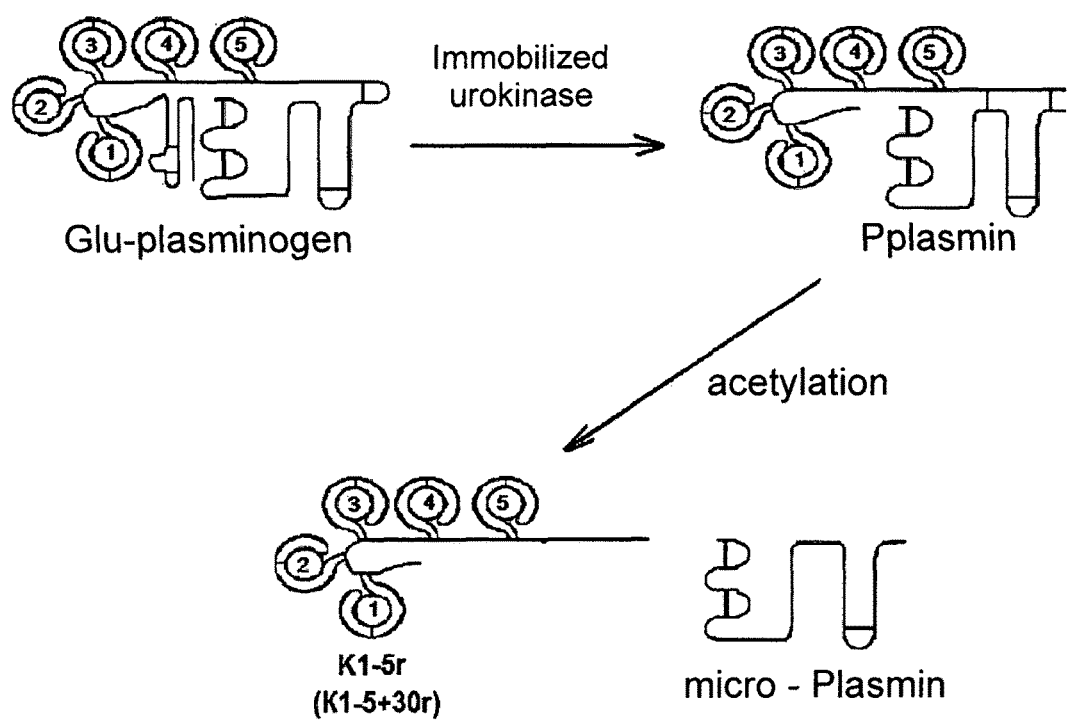

FIG. 2 shows the schematics of the preparation of the heavy chain (Glu-H) Glu1-Arg561 and light chain (L) Val562-Asn791 of human plasminogen

EMBODIMENTS

The plasminogen molecule and fragments thereof, disclosed herein (Table. 1) were obtained either as recombinant proteins or purified from plasma, and used as antigens and detectors to create the immunoassay for the detection of the concentration of proteolytic fragments with a C-terminal lysine in blood samples of patients with various pathologies, including cancer.

Isolation of Ligands for the Immunoassay.

The method for the preparation of the heavy chain (Glu-H) Glu1-Arg561 and light chain (L) Val562-Asn791 of human plasminogen (FIG. 2):

The basic method consists of the activation of plasminogen to plasmin, followed by the reduction of S—S bonds between heavy and light chains in conditions that exclude autolysis, and then isolating the fragments using affinity chromatography on Lys-Sepharose 4B. Urokinase cleaves the Arg561-Val562 bond in plasminogen. The resulting plasmin cuts the 77-78 bond and cleaves off the N-terminal peptide (1-77). Mercaptoethanol reduces the two bonds between Cys558-Cys566 and Cys548-Cys666 which link the heavy and light chains.

First step: Glu-plasminogen was isolated from frozen human donor plasma by affinity chromatography on Lys-Sepharose 4B at 4° C., pH 8.0. Blood plasma was thawed in the presence of aprotinin, centrifuged for 30 min at 4° C. and diluted 2-fold in 0.02 M phosphate buffer, pH 8.0, containing 20 KIU/ml aprotinin. Prepared plasma was then applied onto a Lys-Sepharose 4B column, equilibrated with 0.1 M K-phosphate buffer, pH 8.0, containing 20 KIU/ml aprotinin. The column was washed to remove unbound protein with 0.3 M phosphate buffer, pH 8.0, containing 20 KIU/ml aprotinin, overnight to an absorbance at A280=0.05-0.01. Glu-plasminogen was eluted with a solution of 0.2 M 6-aminocaproic acid in 0.1 M K-phosphate buffer, pH 8.0, containing 20 KIU/ml aprotinin. Fractions containing protein were pooled and subjected to further purification by precipitation $(NH_4)_2SO_4$ (0.31 g/ml protein solution). The precipitate was stored at 4° C. for 18-24 hours and then separated by centrifugation and dissolved in 0.05 M Tris-HCl buffer, pH 8.0 to a concentration 1.5-2.0 mg/ml. The purified Glu-plasminogen was then dialyzed at 4° C. against water (pH 8.0) and lyophilized.

Second step: Urokinase was added to a final concentration of 600 IU/ml to a solution of Glu-plasminogen (5 mg/ml) in 0.05 M Tris-HCl buffer, pH 8.8, containing 0.02 M L-lysine, 0.15 M NaCl, 20% glycerol, and 6000 KIU/ml aprotinin, and incubated for 4 h at 37° C. The progression of conversion of Glu-plasminogen to plasmin was monitored by the hydrolysis of the specific substrate S-2251 (HD-Val-Leu-Lys p-nitroanilide, Sigma, USA) by plasmin in samples from the reaction, with complete conversion identified by observation of the maximum conversion rate for the substrate.

Third step: The reduction of S—S-bonds between the heavy and light chains of plasmin. Mercaptoethanol was added to the plasmin solution to a final concentration of 0.25 mM and incubated under nitrogen in the dark for 20 minutes at room temperature. The resulting free SH-groups were blocked by adding a freshly prepared solution of iodoacetic acid in 0.1 M Na-phosphate buffer, pH 8.0 (to a final concentration of 0.315 M) and incubated for 20 min.

Fourth step: The separation of the heavy and light chains of plasmin by column chromatography on Lys-Sepharose 4B. The reaction mixture was diluted to a concentration of 1 mg/mil of protein with 0.1 M Na-phosphate buffer, pH 8.0, containing 20 KIU/ml aprotinin and applied to a Lys-Sepharose 4B column equilibrated with the same buffer. Chromatography was performed at 25° C. The heavy chain of plasmin, containing kringles K1-5 and 30 amino acid residues of the connecting peptide, was adsorbed onto the sorbent, whereas the light chain was washed away with equilibration buffer. Heavy chain (MR~56-57 kDa) was eluted with a 0.2 M solution of 6-aminocaproic acid in 0.1 M Na-phosphate buffer, pH 8.0. The pooled fractions were dialyzed against water (pH~8.0) and lyophilized.

The purity and molecular weight of the protein were assessed by 12% SDS-polyacrylamide gel electrophoresis. The absence of amidase activity (for S-2251) before and after incubation with urokinase confirmed that the solution of the heavy chain did not contain trace concentrations of miniplasminogen, which may go undetected by electrophoresis.

The purification of Lys-plasminogen (Lys78-Asn791) and its heavy chain (Lys-H Lys78-Arg561) was performed by the same method, but without aprotinin.

Miniplasminogen, which consists of K5 and plasmin light chain (Val442-Asn791), was obtained by incubation of Lys-plasminogen (Lys78-Asn791) with elastase followed by gel filtration on G-75 Sephadex.

The isolation of kringles K1-4, 5 (Lys78-Arg530) was performed according to the method described by Cao and colleagues (Cao R., Wu H. L., Veitonmaki N., Linden P., Farnedo J., Shi C. Y., and Cao Y. 1999. Proc. Natl. Acad. Sci. USA. 96, 5728-5733) with some modifications. Glu-plasminogen (10 mg/ml) was activated with urokinase (600 ME/ml) in 0.05 M phosphate buffer, pH 9.0, containing 0.02 M L-lysine and 0.1 M NaCl, at 37° C. Complete conversion of plasminogen to plasmin was monitored by the increase in the amidase activity of the solution to the maximum activity value. An equal volume of 0.2 M glycerol buffer, pH 12.0 was added to a solution of plasmin, to a final pH of 10.5, and incubated for 18 hours at 25° C. The reaction mixture was diluted 5-fold with buffer containing 0.1 M phosphate buffer, pH 8.0, and 40 KIU/ml aprotinin, and applied to a column of Lys-Sepharose 4B equilibrated with the same buffer. After a washing step, the adsorbed K1-4, 5 was eluted from the column with 0.2 M solution of 6-aminocaproic acid in 0.1 M phosphate buffer, pH 8.0, and 40 KIU/ml aprotinin, dialyzed against water, and lyophilized. The purity of the obtained K1-4, 5 was assessed by 12% SDS-polyacrylamide gel electrophoresis.

a. The isolation of kringle domains K1-4 (Tyr80-Ala440), K1-3 (Tyr80-Val338), and K4-5 (Val355-Phe546) was performed using elastase treatment of Glu-plasminogen by the method described in the work of Cao and colleagues (Cao Y., Ji R. W., Davidson D., Schaller J., Marti D., Sohndel S., McCanse S. G., O'Reilly M. S., Llinas M., and Folkman J. (1996) J. Biol. Chem., 271, 29461-29467). Glu-plasminogen was incubated with elastase at a ratio of 50:1 in a buffer containing 0.05 M Tris-HCl, pH 8.5, 0.5 M NaCl, and 200 KIU aprotinin, for 5 hours at room temperature. The reaction was stopped by adding PMFS to a concentration of 1 mM for 40-50 min. Gel-filtration on a Sephadex G-75 column was performed to separate low and high molecular weight proteins. Protein fractions of the second peak containing K1-3, K1-4, K4-5 and miniplasminogen were applied to Lys-Sepharose 4B affinity column equilibrated with buffer containing 0.05 M Tris-HCl, pH 8.5 and 0.15 M NaCl. After the removal of miniplasminogen which was not adsorbed onto the Lys-Sepharose4B in the flow-through fraction, the adsorbed fragments K1-3, K1-4 and K4-5 were eluted with a solution of 0.2 M 6-aminocaproic acid in the same buffer, dialyzed against a buffer containing 0.02 M Tris-HCl, pH 8.0, and applied to a column of heparin-agarose equilibrated with the same buffer. Unbound fragments K1-4 and K4-5 were eluted with the buffer and fragment K1-3 was eluted with a solution of 0.25 M KCl in the same buffer. The purified fragment K1-3 was dialyzed against water and lyophilized. Fragments K1-4 and K4-5 were separated by gel filtration on Sephadex G-75.

b. Kringles K5 (Ser449 (or Pro452)-Phe546), K1-3 (Tyr80-Val338), and K-4 (Val335-Ala440) were prepared according to the 1997 report from Cao and colleagues (Cao, Y., Chen, A., An, S. S. A., Ji, R. W., Davidson, D., and Llinas, M. (1997) J. Biol. Chem. 272, 22924-22928). The method involves the digestion of Lys-plasminogen (Lys78-Asn791) by elastase. After processing, the elastase mixture was applied to a column of Mono-S (Bio-Rad) equilibrated with buffer containing 20 mM NaOAc, pH 5.0. Fragments of plasminogen were eluted by a gradient of up to 1 M KCl in buffer containing 20 mM NaOAc, pH 5.0. We used KCl gradients of 0-20%, 20-50%, 50-70% and 70-100%. The K-5 fragment eluted at 50%. Fragments containing kringle domain K-4 (Val335-Ala440) and kringle domains K1-3 (Tyr80-Val354) were obtained using a similar scheme, but with a different gradient.

c. The method for the isolation of kringle K5 (Val442-Arg561) involves digesting miniplasminogen (Val442-Asn791) containing K5 within its heavy chain with elastase, followed by digestion of the resulting fragment by pepsin and then using gel filtration and ion exchange chromatography, as described by Thewes and colleagues (Theresa Thewes, Vasudevan Ramesh, Elcna L. Simplaceanu and Miguel Llinfis, Isolation, purification and 1H-NMR characterization of a kringle 5 domain fragment from human plasminogen (Biochimica et BiophysicaActa 912 (1987), 254-269).

d. Kringles K1-4 (Lys78-Pro446) and K-4 (Lys78-Lys468) were prepared according to the method described by Patterson and Sang (Patterson, B. C. and Sang, Q. A. (1997) J. Biol. Chem. 272, 28823-28825), using metalloproteinases. Kringle K1-4 (Asn60-Pro447) was prepared according to the method reported by Lijnen and colleagues (Lijnen, H. R., Ugwu, F., Bini, A., and Collen, D. (1998) Biochemistry 37, 4699-4702), using metalloproteinases.

The Production of a Diagnostic Test System for ELISA to Assay Proteolytic Fragments with a C-Terminal Lysine.

We developed two types of diagnostic systems, direct and inverse.

When preparing a direct diagnostic system, full-length plasminogen or fragments thereof containing at least one kringle domain are used as the ligands for coating the solid phase. The various ligands used in ELISA are listed in Table 1. Their primary amino acid sequences are in the sequence listing.

The ligand was diluted in 0.1M carbonate-bicarbonate buffer, pH 9.6, at a maximum concentration of 5 μg/ml for molecules with a molecular weight greater than 25 kDa, and 10 □g/ml for molecules of mole 1×PBS (phosphate buffered saline): 0.14M NaCl; 0.003MKCl; 0.005M Na2HPO4; 0.002M KH2PO4

Preparation of 1 liter of 10×PBS: NaCl—80 g; KCl—2 g; Na$_2$HPO$_4$—18 g; KH$_2$PO$_4$—2 g Substrate buffer (pH 4.3): 31 mM citric acid, 0.05 N NaOH, H$_2$O$_2$ 3 mM TMB solution: 5 mM 3,3', 5,5'-tetramethylbenzidine in 70% DMSO Chromogenic substrate solution: 4 parts of substrate buffer mixed with 1 part TMB solution.

To create the immunoassay kit, the immobilization of the ligand was preliminarily performed on a solid phase. Various types of carriers for immobilization of a ligand can be used, including cellulose acetate, glass beads or other particles that can adsorb proteins, as well as immunological plates or plastic strips.

100 μL of the ligand solution were added to each well of a microwell plate (Costar). The solution was incubated for 14-16 hours at 4° C. in a humidified chamber. The contents of the wells were removed by shaking out and the plate was then washed twice with a solution containing PBS with 0.05% Tweeen-20 at 200 μL/well to remove unbound ligand. A blocking solution consisting of 200 μL of a 1% solution of bovine serum albumin (BSA) in PBS was added to wells and incubated for 1.5-2 hours at room temperature. After incubation, the blocking solution was removed, the plate dried overnight at room temperature and then used in further applications.

To increase the sensitivity and specificity of the method, a number of components were used in the incubation buffer, as presented in Table 2.

The test and control plasma samples were diluted 100-fold with incubation buffer containing one of the components listed in Table 2, incubated for 1 hour at 37° C. and then diluted with diluent buffer (0.1 M Tris-HCl c 0.05% TWEEN 20, pH 8.0) at a 1:10 dilution, where TWEEN 20 is a brand name for Polysorbate 20, a polysorbate-type nonionic surfactant formed by the ethoxylation of sorbitan before the addition of lauric acid. 100 µL of the solution were added to the appropriate wells and incubated for 1 hour at 37° C. After incubation, the solution was aspirated, the plate was washed 4 times with wash solution (PBS with 0.05% TWEEN 20). A working concentration of the conjugate solution diluted in PBS with 0.5% BSA (Mab Fc IgG-peroxidase or Mab Fc IgA-peroxidase conjugates were used for determination of IgG and IgA levels, respectively) was added to the appropriate wells at 100 µL/well, and incubated for 1 hour at 37° C. Unbound components were removed by washing the plate 4 times with washing solution. 100 µL of the chromogenic substrate-solution were then added to all the wells and incubated for 15 minutes at 37° C. The reaction was stopped by the addition of 100 µL of stop solution (2M $H_2SO_4$). Photometry was performed on an "UNIPLAN" photometer (Pikon, Russia) at a wavelength of 450 nm.

To manufacture the inverse diagnostic system, a labeled full-length plasminogen molecule or fragments thereof, containing at least one kringle domain listed in Table 1 was used as the detector in an ELISA of proteolytic fragments with a C-terminal lysine. The primary amino acid sequences of these peptides are in the sequence listing. To create the inverse diagnostic system (or kit), the first step involved the immobilization of mouse monoclonal antibodies to human immunoglobulins or other proteins onto a solid substrate (solid phase). Several types of immobilization substrates for monoclonal antibodies can be used, such as cellulose acetate, glass beads or other particles that can adsorb proteins, immunological plates or plastic. 100 µL of the monoclonal antibody (10 µg/ml) solution was added to each well of a microtiter plate (Costar). The solution was incubated for 14-16 hours at 4° C. in a humidified chamber. The contents of the wells were removed by shaking out and the plate was then washed twice with a solution containing PBS with 0.05% Tween-20 at 200 µL/well to remove unbound ligand. A blocking solution consisting of 200 µL of a 1% solution of bovine serum albumin (BSA) in PBS was added to wells and incubated for 1.5-2 hours at room temperature. After incubation, the blocking solution was removed, the plate dried overnight at room temperature and then used in further applications.

The full-length plasminogen or fragments thereof were subjected to a biotinylation procedure. 10 mg of a biotinylation reagent, biotinamidohexanoic acid N-hydroxysuccinimide ester (Sigma. B-2643), were dissolved in 0.5 ml of dimethylformamide. Plasminogen or its fragments were dissolved in 0.1 M phosphate buffer, pH 7.4, at a concentration of 1 mg/ml. 5 µl of the biotinylation reagent in dimethylformamide were added to 1 ml of this solution and incubated for 1 hour at room temperature on a shaker. Aprotinin solution was added to a final concentration of 20 IU/ml, the resulting peptide solution was transferred to a dialysis bag (4000 Da) and left overnight to dialyze against 0.01 M phosphate buffer with 20 IU/ml aprotinin, at 4° C. The resulting solution was diluted 2-foldin glycerol and frozen.

To demonstrate the involvement of C-terminal lysines in the protein binding to plasminogen, following incubation with incubation buffer, the plasma samples were diluted to a final dilution of 1:1000 and incubated with carboxypeptidase B (Sigma-Aldrich) at 50 µg/ml in PBS. After incubation with carboxypeptidase B, the enzymatic reaction was stopped the addition of 1,10-Phenathroline (Sigma-Aldrich) in methanol (180 mg/ml). 100 µL of the sample were used for testing in an ELISA assay to determine the concentration of immunoglobulins or other proteins with a C-terminal lysine after proteolysis.

An Immunoassay Method for the Detection of Proteolytic Fragments with a C-Terminal Lysine Blood samples were drawn from the patients' median cubital veins, using EDTA vacutainer tubes. The samples were then centrifuged for 15 min. Plasma was dispensed out into 100 µL aliquots and stored at −40'C.

The control group consisted of plasma samples taken from 5 healthy donors. Each donor sample tested negative for hepatitis A, B, C and HIV viruses, as well as tuberculosis and syphilis.

Titers of proteolytic fragments of immunoglobulins IgG and IgA with C-terminal lysines in control samples were measured using the direct and inverse immunoassay according to the described procedure. The dilution of control samples was selected so that the optical density did not exceed 0.2. For the direct immunoassay, the final dilution of the sample (1:1000) was empirically established, and this dilution was then used for all samples. The full-length plasminogen molecule, as well as its fragments, were used as the ligands. For increased accuracy of measurement, each sample was tested in duplicate. The optical density of the control sample was determined by taking the mean optical density of the pooled samples from 5 healthy controls. The test and control human plasma samples were diluted 100-fold with incubation buffer containing one of the components listed in Table 2, incubated for 1 hour at 37° C., and then diluted with diluent buffer (0.1 M Tris-HCl c 0.05% TWEEN 20, pH 8.0) at a 1:10 dilution. 100 µL of each sample were added to the appropriate wells and incubated for 1 hour at 37° C. After incubation, the solution in the wells was removed and the plate was washed 4 times with wash solution (PBS with 0.05% TWEEN 20). Conjugate solution in PBS with 0.5% BSA (Mab Fc IgG-peroxidase and Mab Fc IgA-peroxidase conjugates were used for determination of IgG and IgA concentrations, respectively) was added to appropriate wells at 100 µL/well, and incubated for 1 hour at 37° C. Unbound components were removed by washing the plate 4 times with washing solution. 100 µL of the chromogenic substrate-solution were then added to all the wells and incubated for 15 minutes at 37° C. The reaction was stopped by adding 100 µL of stop solution (2M $H_2SO_4$). Photometry was performed on an "UNIPLAN" photometer (Pikon, Russia) at a wavelength of 450 nm.

For the inverse immunoassay, the final dilution of the sample (1:1000) was empirically established and used for all samples. A full-length biotinilated molecule of plasminogen as well as its biotinilated fragments were used as detectors. For accuracy of measurement, each sample was tested in duplicate. The optical density of the control sample was determined by obtaining the mean optical density of the pooled samples from five healthy controls. 96-well plates with adsorbed mouse monoclonal antibodies to IgG and IgA (DIATECH-M, Russia) were used.

The test and control human plasma samples were diluted 100-fold with incubation buffer containing one of the components listed in Table 2, incubated for 1 hour at 37° C., and then diluted with diluent buffer (0.1 M Tris-HCl c, 0.05% TWEEN 20, pH 8.0) at a 1:10 dilution. 100 µL of each sample were then added to the appropriate wells and incubated for 1 hour at 37° C. After incubation, the solution in the wells was removed and the plate was washed 4 times with wash solution (PBS with 0.05% TWEEN 20). A working dilution of plasminogen conjugated with biotin or biotinilated fragments thereof, in PBS with 0.5% BSA, were added to appropriate wells at 100 μL/well and incubated for 1 hour at 37° C. Unbound components were removed by washing the plate 4 times using washing solution. 100 μL of streptavidin-peroxidase conjugate solution were then added to all wells and incubated for 30 minutes at 37° C. Unbound components were removed by washing the plate 4 times with washing solution. 100 μL of the chromogenic substrate-solution were then added to all the wells and incubated for 15 minutes at 37° C. The reaction was stopped by adding 100 μL of stop solution (2M $H_2SO_4$). Photometry was performed on an "UNIPLAN" photometer (Pikon, Russia) at a wavelength of 450 nm.

Direct and inverse ELISA of control samples was performed using each individual ligand and biotinylated detector. For comparison, five samples from the healthy control group were taken as controls; these were chosen so that the optical density of each one differed from the group mean by no more than 5%. These 5 samples were pooled and the resulting sample was used as the control sample (C), and was taken to indicate the normal concentration level of immunoglobulins with a C-terminal lysine. The samples with an optical density exceeding that of the control samples by more than 30% were considered positive. This cutoff range avoids false positives.

To evaluate the effectiveness of using various fragments of plasminogen and various organic solvents in the incubation buffer (listed in Table 2), plasma samples of patients with various forms of cancer and autoimmune diseases were used in an ELISA for immunoglobulin fragments with a C-terminal lysine. The examples provided below show the results of using various ligands and detectors in the test system designed to identify high titer of proteolytic fragments of immunoglobulin and other proteins with a C-terminal lysine.

To prove the involvement of C-terminal lysines in the binding to plasminogen or its fragments, plasma samples, after incubation with incubation buffer, were diluted up to a final dilution of 1:1000 and incubated with carboxypeptidase B at a final concentration of 50 mg/ml in PBS (Sigma-Aldrich). After an 1 hour incubation with carboxypeptidase B, the enzymatic reaction was stopped with 1,10-Phenathroline (Sigma-Aldrich) diluted in methanol to a final concentration of 1.8 mg/ml. 100 μL of the sample were used for testing in ELISA to detect the concentration of proteolytic fragments of immunoglobulins and other proteins containing a C-terminal lysine.

EXAMPLES

No difference was observed between the control sample and the sample from a patient in an ELISA for immunoglobulin fragments with a C-terminal lysine when using an incubation buffer without the proposed components listed in Table 2 (dimethylsulfoxide, dimetlformamid, methanol, ethanol, propanol, isopropanol, acetone, acetonitrile, chloroform, ethylene glycol, N-methylpropanamide) at a final dilution of 1:1000. By contrast, when using an incubation buffer with the proposed components listed in Table 2, a clear difference was observed in all cases between the control and the test samples at a final dilution of 1:1000. Notably, after incubation of the samples at a final dilution of 1:1000 with carboxypeptidase B, the difference between the control samples and the patient sample disappeared.

Example 1

Identification of the Binding of IgG and IgA with a C-Terminal Lysine in Prostate Cancer Using Direct ELISA.

Diagnoses of patients with prostate cancer were established on the basis of the following parameters: clinical examination and confirmation by prostate biopsy. The group consisted of 5 patients with prostate cancer.

ELISA of samples from prostate cancer patients and a control sample was performed according to the method described above. The samples where the optical density exceeded the control by more than 30% were considered positive.

Results:

Using the following sequences as the ligand: SEQ ID NO1, SEQ ID NO2, SEQ ID NO3, SEQ ID NO4, SEQ ID NO6, SEQ ID NO9, SEQ ID NO10, SEQ ID NO11, SEQ ID NO12, SEQ ID NO13, in an ELISA, only 2 out of 5 samples from prostate cancer patients were positive for IgG and IgA when using an incubation buffer without the proposed components listed in Table 2. The dilution of samples in this case was 1:100. By contrast, when using an incubation buffer with the proposed components listed in Table 2, the number of positive samples from prostate cancer patients rose to 5 out of 5 positive for IgG and IgA. The final dilution here was 1:1000. After incubation of the samples at a final dilution of 1:1000 with carboxypeptidase B, the difference between the cancer patient samples and the control sample disappeared.

Using the following sequences as the ligand: SEQ ID NO 7, SEQ ID NO8, SEQ ID NO14, SEQ ID NO15, SEQ ID NO16, SEQ ID NO17, SEQ ID NO18, SEQ ID NO19, SEQ ID NO20 in an ELISA, only 2 out of 5 samples from prostate cancer patients were positive for IgG and IgA when using an incubation buffer without the proposed components listed in Table 2. The dilution of samples in this case was 1:100. By contrast, when using an incubation buffer with the proposed components listed in Table 2, the number of positive samples from prostate cancer patients rose to 4 out of 5 positive for IgG and IgA. The final dilution here was 1:1000. After incubation of the samples at a final dilution of 1:1000 with carboxypeptidase B, the difference between the cancer samples and the control sample disappeared.

Example 2

Identification of the Binding of IgG and IgA with a C-Terminal Lysine in Prostate Cancer Using Inverse ELISA.

Diagnoses of patients with prostate cancer were established on the basis of the following parameters: clinical examination and confirmation by prostate biopsy. The group consisted of 5 patients with prostate cancer.

ELISA of samples from prostate cancer patients and a control sample was performed according to the method described above. The samples where the optical density exceeded that of the control sample by more than 30% were considered positive.

Results:

Using the following biotinylated sequences as a detector: SEQ ID NO1, SEQ ID NO2, SEQ ID NO3, SEQ ID NO4, SEQ ID NO6, SEQ ID NO9, SEQ ID NO10, SEQ ID NO11, SEQ ID NO12, SEQ ID NO13 in an ELISA, only 2 out of 5 samples from prostate cancer patients were positive for IgG and IgA using an incubation buffer without the proposed components listed in Table 2. The dilution of samples in this case was 1:100. By contrast, when using an incubation buffer with the proposed components listed in Table 2, the number of positive samples from prostate cancer patients rose to 5 out of 5 positive for IgG and IgA. The final dilution here was 1:1000. After incubation of the samples at a final dilution of 1:1000 with carboxypeptidase B, the difference between the cancer samples and the control sample disappeared.

Using the following biotinylated sequences as a detector: SEQ ID NO7, SEQ ID NO8, SEQ ID NO14, SEQ ID NO15, SEQ ID NO16, SEQ ID NO17, SEQ ID NO18, SEQ ID NO19, SEQ ID NO020, in an ELISA, only 2 out of 5 samples from prostate cancer patients were positive for IgG and IgA using an incubation buffer without the proposed components listed in Table 2. The dilution of samples in this case was 1:100. By contrast, when using an incubation buffer with the proposed components listed in Table 2, the number of positive samples from prostate cancer patients rose to 4 out of 5 positive for IgG and IgA. The final dilution here was 1:1000. After incubation of the samples at a final dilution of 1:1000 with carboxypeptidase B, the difference between the cancer patient samples and the control sample disappeared.

What is claimed is:

1. A method for identifying a subject having an increased blood plasma concentration of proteolytic products having a C-terminal lysine, comprising the following steps:
   providing a human blood plasma sample obtained from a subject;
   contacting the blood plasma sample or a component thereof with a fragment of plasminogen in the presence of a buffer composition, wherein said fragment of plasminogen consists of an amino acid sequence of SEQ ID NO: 1 or SEQ ID NO: 2 or SEQ ID NO: 3 or SEQ ID NO: 4, and
   detecting complexes comprising the fragment of plasminogen bound to the proteolytic product having a C-terminal lysine; and measuring the level of proteolytic products having a C-terminal lysine in the sample;
   wherein an increased amount of complexes or an increased level of proteolytic products having a C-terminal lysine in the sample relative to a control sample is indicative of said human having an increased blood plasma concentration of proteolytic products having a C-terminal lysine.

2. The method of claim 1, wherein an increase of the level of proteolytic products having a C-terminal lysine exceeding the level in the control sample by more than 30% is taken as an indicator of the presence of a prostate cancer in a subject.

3. The method of claim 1 or 2, which comprises the use of an enzyme linked immunosorbent assay (ELISA).

4. The method of claim 1, wherein said contacting comprises contacting the blood plasma sample with a solid support, wherein said fragment of plasminogen SEQ ID NO: 4 is immobilized on the surface of the solid support.

5. The method of claim 1, wherein said contacting comprises (i) contacting the blood plasma sample with a solid support, wherein antibodies specific to the products of proteolysis having a C-terminal lysine are immobilized on the surface of the solid support, (ii) allowing the products of proteolysis having a C-terminal lysine present in the sample to bind to the antibodies, (iii) removing unbound components from the solid support, and (iv) contacting said fragment of plasminogen SEQ ID NO: 4 with the solid support, wherein said fragment of plasminogen SEQ ID NO: 4 is optionally labeled with a detectable label.

6. A test system for identifying a human having an increased concentration of proteolytic products having a C-terminal lysine, comprising a detection system for these products, comprising: a fragment of plasminogen in the presence of a buffer composition, wherein said fragment of plasminogen consists of an amino acid of SEQ ID NO: 1 or SEQ ID NO: 2 or SEQ ID NO: 3 or SEQ ID NO: 4, the fragment of plasminogen contacting with a human blood plasma sample or a component thereof, the test system further comprising a photometer detecting complexes including the fragment of plasminogen bound to a proteolytic product having a C-terminal lysine; the photometer measuring a level of products having a C-terminal lysine; wherein an increased amount of complexes or an increased level of proteolytic products having a C-terminal lysine in a sample relative to a control sample is indicative of said human having an increased blood plasma concentration of proteolytic products having a C-terminal lysine.

7. The test system of claim 6, which comprises the use of an enzyme linked immunosorbent assay (ELISA).

8. The test system of claim 6, further comprising a solid support with said fragment of plasminogen SEQ ID NO: 4 being immobilized on its surface.

9. The test system of claim 6, further comprising a solid support with antibodies specific to the products of proteolysis having a C-terminal lysine mobilized on its surface.

10. The use of a test system according to claim 1 for identifying a subject with a risk of developing a prostate cancer.

11. The method of claim 1, wherein the proteolytic products with C-terminal lysines to be detected are proteolytic fragments of immunoglobulin.

12. The method of claim 11, wherein the proteolytic fragments of immunoglobulin are fragments of IgG and/or fragments of IgA.

13. The method of claim 1, wherein said buffer composition comprises a compound selected from the group consisting of dimethylsulfoxide, dimethylformamide, methanol, ethanol, propanol, propanol-2, acetone, acetonitrile, chloroform, ethylene glycol, N-methylpropanamide and combinations thereof.

14. The test system of claim 6, wherein said buffer composition comprises a compound selected from the group consisting of dimethylsulfoxide, dimethylformamide, methanol, ethanol, propanol, propanol-2, acetone, acetonitrile, chloroform, ethylene glycol, N-methylpropanamide and combinations thereof.

* * * * *

SEQUENCE LISTING

```
<160> NUMBER OF SEQ ID NOS: 20

<210> SEQ ID NO 1
<211> LENGTH: 791
<212> TYPE: PRT
<213> ORGANISM: Homo sapiens

<400> SEQUENCE: 1

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300
```

-continued

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
            645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
            675                 680                 685

Gln Gly Thr Phe Gly Ala Gly Leu Leu Lys Glu Ala Gln Leu Pro Val
            690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser

```
             725                 730                 735
Cys Gln Gly Asp Ser Gly Pro Leu Val Cys Phe Glu Lys Asp Lys
            740                 745                 750

Tyr Ile Leu Gln Gly Val Thr Ser Trp Gly Leu Gly Cys Ala Arg Pro
            755                 760             765

Asn Lys Pro Gly Val Tyr Val Arg Val Ser Arg Phe Val Thr Trp Ile
        770                 775                 780

Glu Gly Val Met Arg Asn Asn
785                 790

<210> SEQ ID NO 2
<211> LENGTH: 714
<212> TYPE: PRT
<213> ORGANISM: Homo sapiens

<400> SEQUENCE: 2

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300
```

```
Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
                420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
                660                 665                 670

Lys Asp Lys Tyr Ile Leu Gln Gly Val Thr Ser Trp Gly Leu Gly Cys
                675                 680                 685

Ala Arg Pro Asn Lys Pro Gly Val Tyr Val Arg Val Ser Arg Phe Val
        690                 695                 700

Thr Trp Ile Glu Gly Val Met Arg Asn Asn
705                 710
```

```
<210> SEQ ID NO 3
<211> LENGTH: 561
<212> TYPE: PRT
<213> ORGANISM: Homo sapiens

<400> SEQUENCE: 3

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380
```

```
Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg

<210> SEQ ID NO 4
<211> LENGTH: 484
<212> TYPE: PRT
<213> ORGANISM: Homo sapiens

<400> SEQUENCE: 4

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175

Tyr Gln Cys Leu Lys Gly Thr Gly Glu Asn Tyr Arg Gly Asn Val Ala
            180                 185                 190
```

```
Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg

<210> SEQ ID NO 5
<211> LENGTH: 230
<212> TYPE: PRT
<213> ORGANISM: Homo sapiens

<400> SEQUENCE: 5

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80
```

Pro Thr Arg Lys Asp Ile Ala Leu Leu Lys Leu Ser Pro Ala Val
            85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
            115                 120                 125

Gly Thr Phe Gly Ala Gly Leu Leu Lys Glu Ala Gln Leu Pro Val Ile
            130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                    165                 170                 175

Gln Gly Asp Ser Gly Gly Pro Leu Val Cys Phe Glu Lys Asp Lys Tyr
                    180                 185                 190

Ile Leu Gln Gly Val Thr Ser Trp Gly Leu Gly Cys Ala Arg Pro Asn
                    195                 200                 205

Lys Pro Gly Val Tyr Val Arg Val Ser Arg Phe Val Thr Trp Ile Glu
            210                 215                 220

Gly Val Met Arg Asn Asn
225                 230

<210> SEQ ID NO 6
<211> LENGTH: 361
<212> TYPE: PRT
<213> ORGANISM: Homo sapiens

<400> SEQUENCE: 6

Tyr Leu Ser Glu Cys Lys Thr Gly Asn Gly Lys Asn Tyr Arg Gly Thr
1               5                   10                  15

Met Ser Lys Thr Lys Asn Gly Ile Thr Cys Gln Lys Trp Ser Ser Thr
            20                  25                  30

Ser Pro His Arg Pro Arg Phe Ser Pro Ala Thr His Pro Ser Glu Gly
        35                  40                  45

Leu Glu Glu Asn Tyr Cys Arg Asn Pro Asp Asn Asp Pro Gln Gly Pro
50                  55                  60

Trp Cys Tyr Thr Thr Asp Pro Glu Lys Arg Tyr Asp Tyr Cys Asp Ile
65                  70                  75                  80

Leu Glu Cys Glu Glu Glu Cys Met His Cys Ser Gly Glu Asn Tyr Asp
                    85                  90                  95

Gly Lys Ile Ser Lys Thr Met Ser Gly Leu Glu Cys Gln Ala Trp Asp
                    100                 105                 110

Ser Gln Ser Pro His Ala His Gly Tyr Ile Pro Ser Lys Phe Pro Asn
                    115                 120                 125

Lys Asn Leu Lys Lys Asn Tyr Cys Arg Asn Pro Asp Arg Glu Leu Arg
            130                 135                 140

Pro Trp Cys Phe Thr Thr Asp Pro Asn Lys Arg Trp Glu Leu Cys Asp
145                 150                 155                 160

Ile Pro Arg Cys Thr Thr Pro Pro Ser Ser Gly Pro Thr Tyr Gln
                    165                 170                 175

Cys Leu Lys Gly Thr Gly Glu Asn Tyr Arg Gly Asn Val Ala Val Thr
                    180                 185                 190

Val Ser Gly His Thr Cys Gln His Trp Ser Ala Gln Thr Pro His Thr
            195                 200                 205

His Asn Arg Thr Pro Glu Asn Phe Pro Cys Lys Asn Leu Asp Glu Asn
            210                 215                 220

Tyr Cys Arg Asn Pro Asp Gly Lys Arg Ala Pro Trp Cys His Thr Thr
225                 230                 235                 240

Asn Ser Gln Val Arg Trp Glu Tyr Cys Lys Ile Pro Ser Cys Asp Ser
            245                 250                 255

Ser Pro Val Ser Thr Glu Gln Leu Ala Pro Thr Ala Pro Pro Glu Leu
        260                 265                 270

Thr Pro Val Val Gln Asp Cys Tyr His Gly Asp Gly Gln Ser Tyr Arg
        275                 280                 285

Gly Thr Ser Ser Thr Thr Thr Gly Lys Lys Cys Gln Ser Trp Ser
    290                 295                 300

Ser Met Thr Pro His Arg His Gln Lys Thr Pro Glu Asn Tyr Pro Asn
305                 310                 315                 320

Ala Gly Leu Thr Met Asn Tyr Cys Arg Asn Pro Asp Ala Asp Lys Gly
            325                 330                 335

Pro Trp Cys Phe Thr Thr Asp Pro Ser Val Arg Trp Glu Tyr Cys Asn
            340                 345                 350

Leu Lys Lys Cys Ser Gly Thr Glu Ala
        355                 360

<210> SEQ ID NO 7
<211> LENGTH: 259
<212> TYPE: PRT
<213> ORGANISM: Homo sapiens

<400> SEQUENCE: 7

Tyr Leu Ser Glu Cys Lys Thr Gly Asn Gly Lys Asn Tyr Arg Gly Thr
1               5                   10                  15

Met Ser Lys Thr Lys Asn Gly Ile Thr Cys Gln Lys Trp Ser Ser Thr
            20                  25                  30

Ser Pro His Arg Pro Arg Phe Ser Pro Ala Thr His Pro Ser Glu Gly
        35                  40                  45

Leu Glu Glu Asn Tyr Cys Arg Asn Pro Asp Asn Asp Pro Gln Gly Pro
    50                  55                  60

Trp Cys Tyr Thr Thr Asp Pro Glu Lys Arg Tyr Asp Tyr Cys Asp Ile
65                  70                  75                  80

Leu Glu Cys Glu Glu Glu Cys Met His Cys Ser Gly Glu Asn Tyr Asp
                85                  90                  95

Gly Lys Ile Ser Lys Thr Met Ser Gly Leu Glu Cys Gln Ala Trp Asp
            100                 105                 110

Ser Gln Ser Pro His Ala His Gly Tyr Ile Pro Ser Lys Phe Pro Asn
        115                 120                 125

Lys Asn Leu Lys Lys Asn Tyr Cys Arg Asn Pro Asp Arg Glu Leu Arg
    130                 135                 140

Pro Trp Cys Phe Thr Thr Asp Pro Asn Lys Arg Trp Glu Leu Cys Asp
145                 150                 155                 160

Ile Pro Arg Cys Thr Thr Pro Pro Pro Ser Ser Gly Pro Thr Tyr Gln
                165                 170                 175

Cys Leu Lys Gly Thr Gly Glu Asn Tyr Arg Gly Asn Val Ala Val Thr
            180                 185                 190

Val Ser Gly His Thr Cys Gln His Trp Ser Ala Gln Thr Pro His Thr
        195                 200                 205

His Asn Arg Thr Pro Glu Asn Phe Pro Cys Lys Asn Leu Asp Glu Asn
    210                 215                 220

Tyr Cys Arg Asn Pro Asp Gly Lys Arg Ala Pro Trp Cys His Thr Thr

```
              225                 230                 235                 240

Asn Ser Gln Val Arg Trp Glu Tyr Cys Lys Ile Pro Ser Cys Asp Ser
                245                 250                 255

Ser Pro Val

<210> SEQ ID NO 8
<211> LENGTH: 275
<212> TYPE: PRT
<213> ORGANISM: Homo sapiens

<400> SEQUENCE: 8

Tyr Leu Ser Glu Cys Lys Thr Gly Asn Gly Lys Asn Tyr Arg Gly Thr
 1               5                  10                  15

Met Ser Lys Thr Lys Asn Gly Ile Thr Cys Gln Lys Trp Ser Ser Thr
             20                  25                  30

Ser Pro His Arg Pro Arg Phe Ser Pro Ala Thr His Pro Ser Glu Gly
         35                  40                  45

Leu Glu Glu Asn Tyr Cys Arg Asn Pro Asp Asn Asp Pro Gln Gly Pro
     50                  55                  60

Trp Cys Tyr Thr Thr Asp Pro Glu Lys Arg Tyr Asp Tyr Cys Asp Ile
 65                  70                  75                  80

Leu Glu Cys Glu Glu Glu Cys Met His Cys Ser Gly Glu Asn Tyr Asp
                 85                  90                  95

Gly Lys Ile Ser Lys Thr Met Ser Gly Leu Glu Cys Gln Ala Trp Asp
            100                 105                 110

Ser Gln Ser Pro His Ala His Gly Tyr Ile Pro Ser Lys Phe Pro Asn
        115                 120                 125

Lys Asn Leu Lys Lys Asn Tyr Cys Arg Asn Pro Asp Arg Glu Leu Arg
    130                 135                 140

Pro Trp Cys Phe Thr Thr Asp Pro Asn Lys Arg Trp Glu Leu Cys Asp
145                 150                 155                 160

Ile Pro Arg Cys Thr Thr Pro Pro Pro Ser Ser Gly Pro Thr Tyr Gln
                165                 170                 175

Cys Leu Lys Gly Thr Gly Glu Asn Tyr Arg Gly Asn Val Ala Val Thr
            180                 185                 190

Val Ser Gly His Thr Cys Gln His Trp Ser Ala Gln Thr Pro His Thr
        195                 200                 205

His Asn Arg Thr Pro Glu Asn Phe Pro Cys Lys Asn Leu Asp Glu Asn
    210                 215                 220

Tyr Cys Arg Asn Pro Asp Gly Lys Arg Ala Pro Trp Cys His Thr Thr
225                 230                 235                 240

Asn Ser Gln Val Arg Trp Glu Tyr Cys Lys Ile Pro Ser Cys Asp Ser
                245                 250                 255

Ser Pro Val Ser Thr Glu Gln Leu Ala Pro Thr Ala Pro Pro Glu Leu
            260                 265                 270

Thr Pro Val
        275

<210> SEQ ID NO 9
<211> LENGTH: 388
<212> TYPE: PRT
<213> ORGANISM: Homo sapiens

<400> SEQUENCE: 9

Asn Arg Lys Ser Ser Ile Ile Ile Arg Met Arg Asp Val Val Leu Phe
 1               5                  10                  15
```

```
Glu Lys Lys Val Tyr Leu Ser Glu Cys Lys Thr Gly Asn Gly Lys Asn
         20                  25                  30

Tyr Arg Gly Thr Met Ser Lys Thr Lys Asn Gly Ile Thr Cys Gln Lys
         35                  40                  45

Trp Ser Ser Thr Ser Pro His Arg Pro Arg Phe Ser Pro Ala Thr His
 50                      55                  60

Pro Ser Glu Gly Leu Glu Glu Asn Tyr Cys Arg Asn Pro Asp Asn Asp
 65                  70                  75                  80

Pro Gln Gly Pro Trp Cys Tyr Thr Thr Asp Pro Glu Lys Arg Tyr Asp
                 85                  90                  95

Tyr Cys Asp Ile Leu Glu Cys Glu Glu Cys Met His Cys Ser Gly
             100                 105                 110

Glu Asn Tyr Asp Gly Lys Ile Ser Lys Thr Met Ser Gly Leu Glu Cys
             115                 120                 125

Gln Ala Trp Asp Ser Gln Ser Pro His Ala His Gly Tyr Ile Pro Ser
 130                     135                 140

Lys Phe Pro Asn Lys Asn Leu Lys Lys Asn Tyr Cys Arg Asn Pro Asp
145                     150                 155                 160

Arg Glu Leu Arg Pro Trp Cys Phe Thr Thr Asp Pro Asn Lys Arg Trp
                 165                 170                 175

Glu Leu Cys Asp Ile Pro Arg Cys Thr Thr Pro Pro Ser Ser Gly
             180                 185                 190

Pro Thr Tyr Gln Cys Leu Lys Gly Thr Gly Glu Asn Tyr Arg Gly Asn
             195                 200                 205

Val Ala Val Thr Val Ser Gly His Thr Cys Gln His Trp Ser Ala Gln
 210                     215                 220

Thr Pro His Thr His Asn Arg Thr Pro Glu Asn Phe Pro Cys Lys Asn
225                     230                 235                 240

Leu Asp Glu Asn Tyr Cys Arg Asn Pro Asp Gly Lys Arg Ala Pro Trp
                 245                 250                 255

Cys His Thr Thr Asn Ser Gln Val Arg Trp Glu Tyr Cys Lys Ile Pro
             260                 265                 270

Ser Cys Asp Ser Ser Pro Val Ser Thr Glu Gln Leu Ala Pro Thr Ala
             275                 280                 285

Pro Pro Glu Leu Thr Pro Val Val Gln Asp Cys Tyr His Gly Asp Gly
 290                     295                 300

Gln Ser Tyr Arg Gly Thr Ser Ser Thr Thr Thr Gly Lys Lys Cys
305                     310                 315                 320

Gln Ser Trp Ser Ser Met Thr Pro His Arg His Gln Lys Thr Pro Glu
                 325                 330                 335

Asn Tyr Pro Asn Ala Gly Leu Thr Met Asn Tyr Cys Arg Asn Pro Asp
             340                 345                 350

Ala Asp Lys Gly Pro Trp Cys Phe Thr Thr Asp Pro Ser Val Arg Trp
             355                 360                 365

Glu Tyr Cys Asn Leu Lys Lys Cys Ser Gly Thr Glu Ala Ser Val Val
             370                 375                 380

Ala Pro Pro Pro
385

<210> SEQ ID NO 10
<211> LENGTH: 370
<212> TYPE: PRT
<213> ORGANISM: Homo sapiens
```

<400> SEQUENCE: 10

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro
    370

<210> SEQ ID NO 11
<211> LENGTH: 369
<212> TYPE: PRT
<213> ORGANISM: Homo sapiens
```

<400> SEQUENCE: 11

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro
```

<210> SEQ ID NO 12
<211> LENGTH: 391
<212> TYPE: PRT
<213> ORGANISM: Homo sapiens

<400> SEQUENCE: 12

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
        370                 375                 380

Cys Met Phe Gly Asn Gly Lys
385                 390
```

<210> SEQ ID NO 13
<211> LENGTH: 453
<212> TYPE: PRT
<213> ORGANISM: Homo sapiens

<400> SEQUENCE: 13

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380
```

```
Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
            405                 410                 415

His Ser Ile Phe Thr Pro Glu Thr Asn Pro Arg Ala Gly Leu Glu Lys
        420                 425                 430

Asn Tyr Cys Arg Asn Pro Asp Gly Asp Val Gly Gly Pro Trp Cys Tyr
        435                 440                 445

Thr Thr Asn Pro Arg
        450
```

<210> SEQ ID NO 14
<211> LENGTH: 192
<212> TYPE: PRT
<213> ORGANISM: Homo sapiens

<400> SEQUENCE: 14

```
Val Gln Asp Cys Tyr His Gly Asp Gly Gln Ser Tyr Arg Gly Thr Ser
1               5                   10                  15

Ser Thr Thr Thr Thr Gly Lys Lys Cys Gln Ser Trp Ser Ser Met Thr
            20                  25                  30

Pro His Arg His Gln Lys Thr Pro Glu Asn Tyr Pro Asn Ala Gly Leu
        35                  40                  45

Thr Met Asn Tyr Cys Arg Asn Pro Asp Ala Asp Lys Gly Pro Trp Cys
    50                  55                  60

Phe Thr Thr Asp Pro Ser Val Arg Trp Glu Tyr Cys Asn Leu Lys Lys
65                  70                  75                  80

Cys Ser Gly Thr Glu Ala Ser Val Val Ala Pro Pro Val Val Leu
                85                  90                  95

Leu Pro Asp Val Glu Thr Pro Ser Glu Glu Asp Cys Met Phe Gly Asn
            100                 105                 110

Gly Lys Gly Tyr Arg Gly Lys Arg Ala Thr Thr Val Thr Gly Thr Pro
        115                 120                 125

Cys Gln Asp Trp Ala Ala Gln Glu Pro His Arg His Ser Ile Phe Thr
    130                 135                 140

Pro Glu Thr Asn Pro Arg Ala Gly Leu Glu Lys Asn Tyr Cys Arg Asn
145                 150                 155                 160

Pro Asp Gly Asp Val Gly Gly Pro Trp Cys Tyr Thr Thr Asn Pro Arg
                165                 170                 175

Lys Leu Tyr Asp Tyr Cys Asp Val Pro Gln Cys Ala Ala Pro Ser Phe
            180                 185                 190
```

<210> SEQ ID NO 15
<211> LENGTH: 85
<212> TYPE: PRT
<213> ORGANISM: Homo sapiens

<400> SEQUENCE: 15

```
Tyr Leu Ser Glu Cys Lys Thr Gly Asn Gly Lys Asn Tyr Arg Gly Thr
1               5                   10                  15

Met Ser Lys Thr Lys Asn Gly Ile Thr Cys Gln Lys Trp Ser Ser Thr
            20                  25                  30

Ser Pro His Arg Pro Arg Phe Ser Pro Ala Thr His Pro Ser Glu Gly
        35                  40                  45

Leu Glu Glu Asn Tyr Cys Arg Asn Pro Asp Asn Asp Pro Gln Gly Pro
    50                  55                  60
```

Trp Cys Tyr Thr Thr Asp Pro Glu Lys Arg Tyr Asp Tyr Cys Asp Ile
65                  70                  75                  80

Leu Glu Cys Glu Glu
                85

<210> SEQ ID NO 16
<211> LENGTH: 173
<212> TYPE: PRT
<213> ORGANISM: Homo sapiens

<400> SEQUENCE: 16

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys Thr Thr
65                  70                  75                  80

Pro Pro Pro Ser Ser Gly Pro Thr Tyr Gln Cys Leu Lys Gly Thr Gly
                85                  90                  95

Glu Asn Tyr Arg Gly Asn Val Ala Val Thr Val Ser Gly His Thr Cys
            100                 105                 110

Gln His Trp Ser Ala Gln Thr Pro His Thr His Asn Arg Thr Pro Glu
        115                 120                 125

Asn Phe Pro Cys Lys Asn Leu Asp Glu Asn Tyr Cys Arg Asn Pro Asp
    130                 135                 140

Gly Lys Arg Ala Pro Trp Cys His Thr Thr Asn Ser Gln Val Arg Trp
145                 150                 155                 160

Glu Tyr Cys Lys Ile Pro Ser Cys Asp Ser Ser Pro Val
                165                 170

<210> SEQ ID NO 17
<211> LENGTH: 86
<212> TYPE: PRT
<213> ORGANISM: Homo sapiens

<400> SEQUENCE: 17

Val Gln Asp Cys Tyr His Gly Asp Gly Gln Ser Tyr Arg Gly Thr Ser
1               5                   10                  15

Ser Thr Thr Thr Thr Gly Lys Lys Cys Gln Ser Trp Ser Ser Met Thr
            20                  25                  30

Pro His Arg His Gln Lys Thr Pro Glu Asn Tyr Pro Asn Ala Gly Leu
        35                  40                  45

Thr Met Asn Tyr Cys Arg Asn Pro Asp Ala Asp Lys Gly Pro Trp Cys
    50                  55                  60

Phe Thr Thr Asp Pro Ser Val Arg Trp Glu Tyr Cys Asn Leu Lys Lys
65                  70                  75                  80

Cys Ser Gly Thr Glu Ala
                85

<210> SEQ ID NO 18
<211> LENGTH: 106
<212> TYPE: PRT
<213> ORGANISM: Homo sapiens -continued

<400> SEQUENCE: 18

Ser Val Val Ala Pro Pro Val Val Leu Leu Pro Asp Val Glu Thr
1               5                   10                  15

Pro Ser Glu Glu Asp Cys Met Phe Gly Asn Gly Lys Gly Tyr Arg Gly
            20                  25                  30

Lys Arg Ala Thr Thr Val Thr Gly Thr Pro Cys Gln Asp Trp Ala Ala
        35                  40                  45

Gln Glu Pro His Arg His Ser Ile Phe Thr Pro Glu Thr Asn Pro Arg
    50                  55                  60

Ala Gly Leu Glu Lys Asn Tyr Cys Arg Asn Pro Asp Gly Asp Val Gly
65                  70                  75                  80

Gly Pro Trp Cys Tyr Thr Thr Asn Pro Arg Lys Leu Tyr Asp Tyr Cys
                85                  90                  95

Asp Val Pro Gln Cys Ala Ala Pro Ser Phe
            100                 105

<210> SEQ ID NO 19
<211> LENGTH: 120
<212> TYPE: PRT
<213> ORGANISM: Homo sapiens

<400> SEQUENCE: 19

Val Val Ala Pro Pro Val Val Leu Leu Pro Asp Val Glu Thr Pro
1               5                   10                  15

Ser Glu Glu Asp Cys Met Phe Gly Asn Gly Lys Gly Tyr Arg Gly Lys
            20                  25                  30

Arg Ala Thr Thr Val Thr Gly Thr Pro Cys Gln Asp Trp Ala Ala Gln
        35                  40                  45

Glu Pro His Arg His Ser Ile Phe Thr Pro Glu Thr Asn Pro Arg Ala
    50                  55                  60

Gly Leu Glu Lys Asn Tyr Cys Arg Asn Pro Asp Gly Asp Val Gly Gly
65                  70                  75                  80

Pro Trp Cys Tyr Thr Thr Asn Pro Arg Lys Leu Tyr Asp Tyr Cys Asp
                85                  90                  95

Val Pro Gln Cys Ala Ala Pro Ser Phe Asp Cys Gly Lys Pro Gln Val
            100                 105                 110

Glu Pro Lys Lys Cys Pro Gly Arg
        115                 120

<210> SEQ ID NO 20
<211> LENGTH: 350
<212> TYPE: PRT
<213> ORGANISM: Homo sapiens

<400> SEQUENCE: 20

Val Val Ala Pro Pro Val Val Leu Leu Pro Asp Val Glu Thr Pro
1               5                   10                  15

Ser Glu Glu Asp Cys Met Phe Gly Asn Gly Lys Gly Tyr Arg Gly Lys
            20                  25                  30

Arg Ala Thr Thr Val Thr Gly Thr Pro Cys Gln Asp Trp Ala Ala Gln
        35                  40                  45

Glu Pro His Arg His Ser Ile Phe Thr Pro Glu Thr Asn Pro Arg Ala
    50                  55                  60

Gly Leu Glu Lys Asn Tyr Cys Arg Asn Pro Asp Gly Asp Val Gly Gly
65                  70                  75                  80

Pro Trp Cys Tyr Thr Thr Asn Pro Arg Lys Leu Tyr Asp Tyr Cys Asp

```
                        85                     90                      95
Val Pro Gln Cys Ala Ala Pro Ser Phe Asp Cys Gly Lys Pro Gln Val
            100                    105                    110

Glu Pro Lys Lys Cys Pro Gly Arg Val Val Gly Gly Cys Val Ala His
            115                    120                    125

Pro His Ser Trp Pro Trp Gln Val Ser Leu Arg Thr Arg Phe Gly Met
            130                    135                    140

His Phe Cys Gly Gly Thr Leu Ile Ser Pro Glu Trp Val Leu Thr Ala
145                    150                    155                    160

Ala His Cys Leu Glu Lys Ser Pro Arg Pro Ser Ser Tyr Lys Val Ile
            165                    170                    175

Leu Gly Ala His Gln Glu Val Asn Leu Glu Pro His Val Gln Glu Ile
            180                    185                    190

Glu Val Ser Arg Leu Phe Leu Glu Pro Thr Arg Lys Asp Ile Ala Leu
            195                    200                    205

Leu Lys Leu Ser Ser Pro Ala Val Ile Thr Asp Lys Val Ile Pro Ala
            210                    215                    220

Cys Leu Pro Ser Pro Asn Tyr Val Val Ala Asp Arg Thr Glu Cys Phe
225                    230                    235                    240

Ile Thr Gly Trp Gly Glu Thr Gln Gly Thr Phe Gly Ala Gly Leu Leu
            245                    250                    255

Lys Glu Ala Gln Leu Pro Val Ile Glu Asn Lys Val Cys Asn Arg Tyr
            260                    265                    270

Glu Phe Leu Asn Gly Arg Val Gln Ser Thr Glu Leu Cys Ala Gly His
            275                    280                    285

Leu Ala Gly Gly Thr Asp Ser Cys Gln Gly Asp Ser Gly Gly Pro Leu
            290                    295                    300

Val Cys Phe Glu Lys Asp Lys Tyr Ile Leu Gln Gly Val Thr Ser Trp
305                    310                    315                    320

Gly Leu Gly Cys Ala Arg Pro Asn Lys Pro Gly Val Tyr Val Arg Val
            325                    330                    335

Ser Arg Phe Val Thr Trp Ile Glu Gly Val Met Arg Asn Asn
            340                    345                    350
```